United States Patent [19]

Ribaldone et al.

[11] 4,048,173
[45] Sept. 13, 1977

[54] HETEROCYCLIC POLYNUCLEAR PIGMENTS AND PROCESS FOR PREPARING SAME

[75] Inventors: Giuseppe Ribaldone, Gallarate (Varese); Giampiero Borsotti, Novara, both of Italy

[73] Assignee: Montedison S.p.A., Milan, Italy

[21] Appl. No.: 663,151

[22] Filed: Mar. 2, 1976

[30] Foreign Application Priority Data

Mar. 6, 1975  Italy .................................. 20988/75

[51] Int. Cl.² .............................................. C09B 5/14
[52] U.S. Cl. .................................. 260/272; 260/278; 106/288 Q
[58] Field of Search ................... 260/272, 289 C, 278

*Primary Examiner*—Donald G. Daus
*Assistant Examiner*—D. B. Springer
*Attorney, Agent, or Firm*—Stevens, Davis, Miller & Mosher

[57] ABSTRACT

New compounds are disclosed having the general formula:

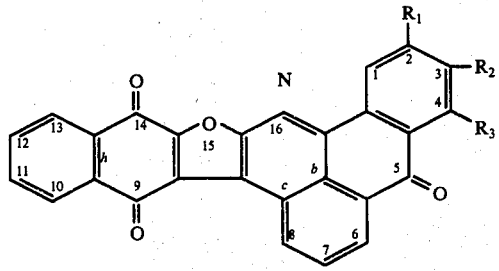

wherein $R_1$, $R_2$ and $R_3$ may be the same or different and are selected from the class consisting of H, Cl and $OCH_3$. They are useful as pigments. They are prepared by reacting a substituted or unsubstituted 1-aza-2-hydroxybenzanthrone with 2,3-dichloro-1,4-naphthoquinone, in the presence of pyridine, at a temperature between 80° and about 120° C.

7 Claims, No Drawings

HETEROCYCLIC POLYNUCLEAR PIGMENTS AND PROCESS FOR PREPARING SAME

This invention relates to a new class of heterocyclic polynuclear compounds, and to a method of preparing same.

This class of compounds is represented by the following general formula;

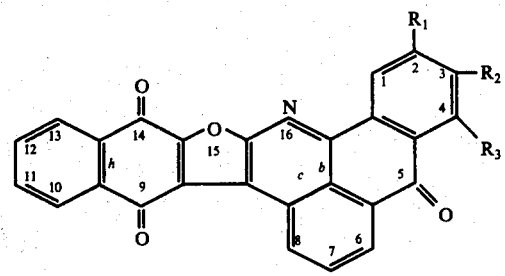

(I)

wherein $R_1$, $R_2$, $R_3$ may be the same or different and are selected from H, Cl and $OHC_3$.

When $R_1$, $R_2$, $R_3$ = H, the compound may be defined as 5,9,14-trioxo, 15-oxa, 16-aza-anthra[b,c]-benzo[h]-fluorene.

These compounds have a color varying from red to yellow depending upon the substituents $R_1$, $R_2$, $R_3$. By virtue of their excellent stability, they are particularly useful as pigments.

A further feature of the present invention resides in the fact that the compounds in question are easily prepared by condensing, in the presence of pyridine, 1-aza-2-hydroxybenzanthrone (II), or its substituted derivatives, with 2,3-dichloro-1,4-naphthoquinone (III) according to the following reaction:

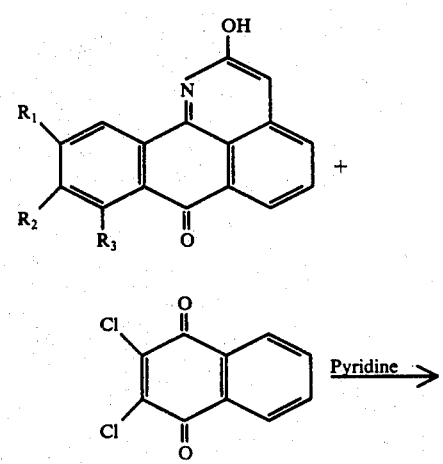

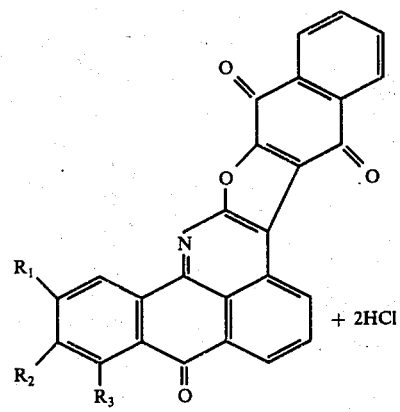

where $R_1$, $R_2$, $R_3$ have the meanings specified hereinbefore.

The substituted derivatives of 1-aza-2-hydroxybenzathrone (II) readily employable according to this invention include, for example, the following:

1-aza-2-hydroxy-8-chlorobenzanthrone;
1-aza-2-hydroxy-9,10-dichlorobenzanthrone;
1-aza-2-hydroxy-8-methoxybenzanthrone.

The starting materials necessary to practice the present invention are readily available, because 2,3-dichloro-1,4-naphthoquinone (III) is a commercial product existing on the market while 1-aza-2-hydroxybenzanthrone (II) is easily obtained from 1-aminoanthraquinone according to the method described in Italian Pat. No. 955,384 and in Italian Patent Application No. 26722 A/73corresponding to Belgian Pat. No. 817,725.

Compound (II) is obtained according to the following process: Anthraquinone-1-diazonium sulphates (either simple or substituted by $R_1$, $R_2$ and $R_3$ defined as above) are reacted with 1,1-dichloro-ethylene in the presence of cuprous salts, and especially cuprous halides such as the chloride, bromide and iodide, and of alcohols (e.g., $CH_3OH$), thus obtaining the esters of anthraquinone-1-acetic acid (Italian Pat. No. 955,384). These esters, by treatment with ammonia in a hydroxylated solvent ($CH_3OH$; $H_2O$), in the presence of strong bases and/or reducing agents (e.g., zinc powder), are converted into intermediate compound (II) (Belgian Pat. No. 817,725).

With regard to derivatives of 1-aza-2-hydroxy-benzanthrone, i.e., where $R_1$, $R_2$ and/or $R_3$ are different from H, although these have not been exemplified in the above-cited patents and patent application, nevertheless they can be readily prepared starting from the corresponding substituted 1-amino-anthraquinones by proceeding in an otherwise similar way.

Thus, it is an object of the present invention to provide a new class of compounds having useful applications in the pigments field.

This and still other objects, which will become more clearly apparent to those skilled in the art from the following description, are achieved by a process for preparing compounds having formula (I), characterized in that 1-aza-2-hydroxybenzanthrone (II) is reacted with 2,3-dichloro-1,4-naphthoquinone (III) in the presence of pyridine at a temperature ranging from 80° to about 120° C.

The molar ratio between the two reagents is essentially stoichiometric, but it is preferable to employ a slight excess (5-15%) of the 2,3-dichloro-1,4-naphthoquinone.

Depending on the particular temperature employed, the reaction time may range from 2 to about 5 hours.

Pyridine is used in an amount sufficient to insure that the reaction mixture can be easily stirred. In practice, at least 10 parts of pyridine per part of 1-aza-2-hydroxybenzanthrone compound are employed. Parts are intended by weight.

In carrying out the reaction it is advantageous to utilize pyridine because, besides being a good solvent for the reagents, this is also capable of neutralizing the hydrochloric acid evolved during the reaction.

According to the particularly useful embodiment of this invention, for example, it is practiced as follows: 1-aza-2-hydroxybenzanthrone or its substituted derivatives and 2,3-dichloro-1,4-naphthoquinone are heated under stirring in the presence of pyridine to a temperature ranging from 80° to 120° C for a reaction time of 2 to 5 hours. At the conclusion of the reaction, the reaction mixture containing the condensation product in suspension is filtered, without prior cooling. The filtered condensation product is washed at first with pyridine, or with dimethylformamide, in which it is practically insoluble, then with water and at least (optionally) with acetone.

Due to the mild operating conditions, the process is particularly advantageous. Additional advantages consist in that the new pigments obtained according to the present invention exhibit excellent properties, such as stability to sunlight, to elevated temperatures, and to solvents, and in consequence, they may be used for the mass coloring of plastic materials such as polystyrene, polyvinyl chloride, polyamides, polyesters, polyacrylonitrile, cellulose acetates, etc.

Furthermore they may be used in the preparation of paints and printing inks.

The following examples are given to still better illustrate the invention, without however limiting same. Example 2 includes also the preparation of starting intermediates according to techniques cited above. Furthermore, Example 5 illustrates a typical application of the novel compounds of this invention.

EXAMPLE 1

A mixture consisting of 20 g of 1-aza-2-hydroxybenzanthrone, 20 g of 2,3-dichloro-1,4-naphthoquinone, and 320 cc of pyridine was heated at reflux and under stirring for 2 hours. It was then cooled down to room temperature, whereupon the solid product was filtered, washed with dimethylformamide, then with water and finally with acetone.

After drying, there was obtained 27 g of an orange pigment having the following structural formula:

Elemental analysis, the IR-spectrum and the mass spectrum all corresponded to the above structural formula of the compound thus obtained.

EXAMPLE 2

1. Preparation of 5-chloro-anthraquinone-1-methyl acetate 22 g of sodium nitrite were added, under stirring, in 15 minutes, to 300 cc of concentrated sulphuric acid. After obtaining a homogeneous solution, 55 g of 1-amino-5-chloroanthraquinone were added in 1 hour, keeping the temperature at 30° C. The mixture then was heated to 50° C for about 20 minutes, then it was cooled to 30° C, and the solution was gradually poured onto 600 g of ice.

The precipitated diazonium salt, after filtering and washing with methanol, was added to a mixture made up of 500 cc of methanol and 200 cc of 1,1-dichloroethylene. The mixture was stirred at 30° C, 5 g of hydrochloric acid in 20 cc of methanol were added, and then cuprous chloride in portions of 50 mg each, until nitrogen began to evolve. (Total amount of added cuprous chloride: about 0.25 g.)

The reaction was exothermic and the temperature was kept at 30°-35° C by means of cooling. Nitrogen evolution stopped after about 30 minutes and a precipitate of 5-chloroanthraquinone-1-methylacetate began to form. This was followed by heating at reflux for about 30 minutes, whereupon both 1,1-dichloro-ethylene and methanol distilled, until the vapors reached 65° C. After cooling to 20° C, the precipitate was filtered and washed with methanol to neutrality. 60 g of 5-chloroanthraquinone-1-methylacetate were thus obtained after drying.

2. Preparation of 1-aza-2-hydroxy-8-chlorobenzanthrone 60 g of ammonia were absorbed in 300 cc of methanol, cooled down to −10° C, then 30 g of 5-chloroanthraquinone-1-methylacetate and 1 g of zinc powder were added thereto. The mixture was kept under stirring for about 5 hours at room temperature and at a pressure of 1.4 kg/cm². It was heated to 60° C to remove ammonia, diluted with 2 l of methanol, rendered alkaline with 25 g of 50% NaOH, heated to 60° C for about 20 minutes, and filtered on kieselguhr. The filtered solution was diluted with 1 l of water and acidified with concentrated hydrochloric acid.

The resulting yellow-colored precipitate was filtered and then washed with water to neutrality.

After drying, there was obtained 23.4 g of 1-aza-2-hydroxy-8-chlorobenzanthrone having the structural formula:

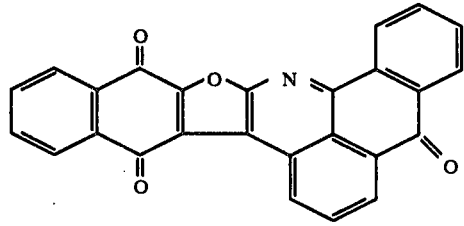

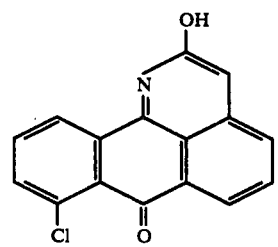

3. Preparation of the pigment according to this invention

A mixture consisting of 20 g of 1-aza-2-hydroxy-8-chlorobenzanthrone obtained as described above, 17.6 g of 2,3-dichloro-1,4-naphthoquinone, and 320 cc of pyridine was heated at reflux and under stirring for about 3 hours. At the conclusion of the reaction, it was hot-filtered and the solid product obtained was washed successively with pyridine, hot water, dimethylformamide and, finally, acetone.

After drying, there was obtained 26.4 g of an orange pigment having the following structural formula:

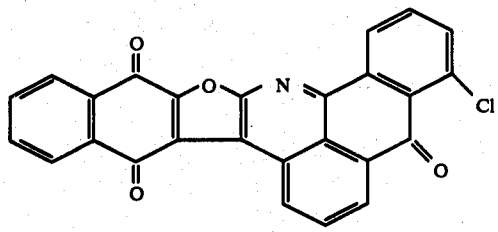

This corresponds to formula (I) where $R_1 = R_2 = H$ and $R_3 = Cl$.

Elemental analysis, the IR-spectrum and the mass spectrum of the products obtained as described above corresponded to the formulas given.

EXAMPLE 3

Operating according to the procedure described above in Example 2 but using 1-amino-6,7-dichloroanthraquinone as starting reactant, 1-aza-2-hydroxy-9,10-dichlorobenzanthrone was obtained, an orange powder having the following structural formula:

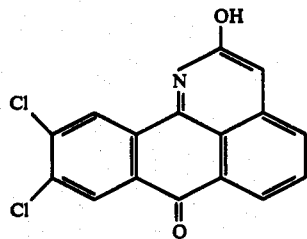

A mixture consisting of 22.4 g of 1-aza-2-hydroxy-9,10-dichlorobenzanthrone, 17.6 g of 2,3-dichloro-1,4-naphthoquinone, and 600 cc of pyridine was heated at reflux for about 3 hours. On completion of the reaction, it was hot-filtered and the resulting solid product was washed successively with pyridine, hot water, dimethylformamide and, finally, acetone.

After drying, there was obtained 24.8 g of an orange pigment having the following structural formula:

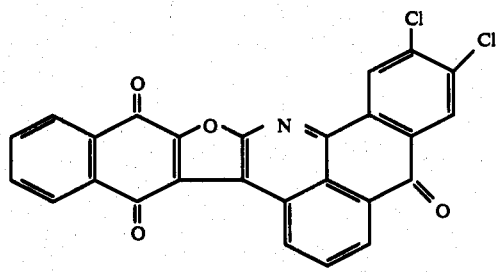

wherein $R_1$, $R_2$ of formula (I) = Cl and $R_3$ = H.

Elemental analysis, the IR-spectrum and the mass spectrum of the products so obtained corresponded to the formulas given.

EXAMPLE 4

Operating according to the procedure described above in Example 2 but employing 1-amino-5-methoxyanthraquinone as starting reactant, 1-aza-2-hydroxy-8-methoxybenzanthrone was obtained, a yellow-colored powder having the following structural formula:

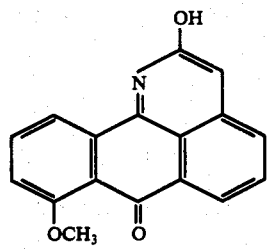

A mixture consisting of 25 g of 1-aza-2-hydroxy-8-methoxybenzanthrone, 23 g of 2,3-dichloro-1,4-naphthoquinone, and 400 cc of pyridine was heated at reflux for about 3 hours. At the conclusion of the reaction it was cooled down to room temperature, and the solid product filtered, washed with pyridine, hot water, dimethylformamide and, finally, acetone.

After drying, there was obtained 25 g of a red pigment having the following structural formula:

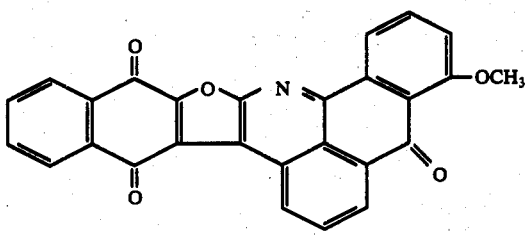

wherein $R_3$ of formula (I) = $OCH_3$ and $R_1 = R_2 = H$.

Elemental analysis, the IR-spectrum and the mass spectrum of the products so obtained corresponded to the formulas given.

EXAMPLE 5

Dyeing of plastic materials and paint compositions with the pigments obtained as described in the preceding examples was readily carried out by incorporating same therein by means of suitable well-known mixing, blending and kneading equipment, such as the three-cylinder refiner, the disk mill, etc., according to per se conventional techniques.

In applications with polyvinyl chloride for making plasticized shaped articles, the PVC resin in powder form was hot-mixed (70° C) in a rotating arm mixer with the necessary and conventional amounts of plasticizers, stabilizers, fillers and the pigment.

Operating according to techniques and recipes already per se known, the following materials were treated at 180° C in a three-cylinder refiner until thorough dispersion of the pigment was effected:

100 g of polyvinyl chloride;

1.5 g of a Ba or Cd complex salt of a higher fatty acid (stearic acid) having a complex and antioxidizing action;

3 g of epoxidized soybean oil;

0.5 g of lubricant (glycerides from $C_{16}$ to $C_{36}$);

2 g of $TiO_2$; and 1 g of pigment prepared according to Example 1.

A plastic sheet having an orange shade and exhibiting excellent fastness to sunlight and to solvents as well as excellent thermostability was thus obtained.

The pigment prepared according to Example 1, when incorporated in polystyrene, imparts a bright yellow dyeing thereto.

Analogous results were obtained by employing the pigments produced according to Examples 2, 3 and 4 in an otherwise similar manner.

What is claimed is:

1. A compound having the formula:

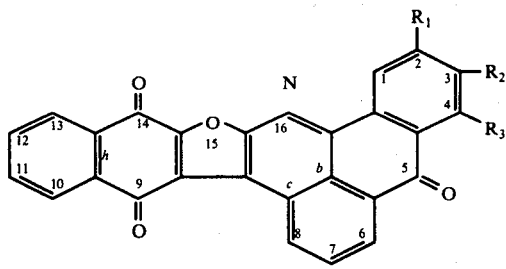

wherein $R_1$, $R_2$ and $R_3$ may be the same or different and are selected from the class consisting of H, Cl and $OCH_3$.

2. A compound of claim 1, wherein $R_1 = R_2 = R_3 = H$.

3. A compound of claim 1, wherein $R_1 = R_2 = H$ and $R_3 = Cl$.

4. A compound of claim 1, wherein $R_1 = R_2 = Cl$ and $R_3 = H$.

5. A compound of claim 1, wherein $R_1 = R_2 = H$ and $R_3 = OCH_3$.

6. A process for preparing a compound having the formula of claim 1, characterized in that a substituted or unsubstituted 1-aza-2-hydroxybenzanthrone is reacted with 2,3-dichloro-1,4-naphthoquinone in the presence of pyridine at a temperature between 80° and about 120° C, a substantially stoichiometric molar ratio of the reactants being employed.

7. A process according to claim 6, wherein the pyridine is employed in an amount, with respect to the substituted or unsubstituted 1-aza-2-hydroxybenzanthrone, which corresponds to about 10 : 1 by weight.

* * * * *